United States Patent
Kim et al.

(10) Patent No.: US 11,517,258 B2
(45) Date of Patent: Dec. 6, 2022

(54) ELECTRONIC DEVICE FOR PROVIDING INFORMATION REGARDING EXERCISE STATE BASED ON METABOLITE INFORMATION AND METHOD THEREOF

(71) Applicant: Samsung Electronics Co., Ltd., Suwon-si (KR)

(72) Inventors: Minji Kim, Suwon-si (KR); Hyejung Seo, Suwon-si (KR); Seunggoo Lee, Suwon-si (KR); Taehan Jeon, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 181 days.

(21) Appl. No.: 16/371,649

(22) Filed: Apr. 1, 2019

(65) Prior Publication Data

US 2019/0298258 A1  Oct. 3, 2019

(30) Foreign Application Priority Data

Apr. 2, 2018 (KR) .................. 10-2018-0037903

(51) Int. Cl.
*A61B 5/00* (2006.01)
*A61B 5/103* (2006.01)
(Continued)

(52) U.S. Cl.
CPC ........ *A61B 5/4866* (2013.01); *A61B 5/02416* (2013.01); *A61B 5/1032* (2013.01);
(Continued)

(58) Field of Classification Search
CPC combination set(s) only.
See application file for complete search history.

(56) References Cited

U.S. PATENT DOCUMENTS 9,427,191 B2  8/2016  Leboeuf
9,445,749 B2  9/2016  Erickson et al.
(Continued)

FOREIGN PATENT DOCUMENTS

EP  3258846 A1  6/2017
JP  2014-226417 A  12/2014
(Continued)

OTHER PUBLICATIONS

International Search Report dated Jul. 19, 2019, issued in an International application No. PCT/KR2019/003786.
(Continued)

*Primary Examiner* — Gary Jackson
*Assistant Examiner* — Zahed Kabir
(74) *Attorney, Agent, or Firm* — Jefferson IP Law, LLP

(57) ABSTRACT

An electronic device for providing exercise information and a method therefor are provided. The electronic device includes a first sensor module, a second sensor module, at least one output device, and at least one processor. The at least one processor is configured to detect an event relating to start of an exercise state, obtain motion information corresponding to the exercise state using the first sensor module, obtain metabolite information of a user using the second sensor module, and provide information regarding the exercise state to the user through the at least one output device, based on whether the metabolite information satisfies a specified condition.

18 Claims, 11 Drawing Sheets

(51) Int. Cl.

| | |
|---|---|
| *A61B 5/1486* | (2006.01) |
| *A63B 24/00* | (2006.01) |
| *A61B 5/024* | (2006.01) |
| *A61B 5/11* | (2006.01) |
| *G16H 20/30* | (2018.01) |
| *G16H 50/30* | (2018.01) |
| *G16H 40/63* | (2018.01) |

(52) U.S. Cl.
CPC .......... *A61B 5/1118* (2013.01); *A61B 5/1486* (2013.01); *A61B 5/7475* (2013.01); *A63B 24/0062* (2013.01); *G16H 20/30* (2018.01); *G16H 40/63* (2018.01); *G16H 50/30* (2018.01); *A61B 2562/0219* (2013.01); *A63B 2024/0068* (2013.01); *A63B 2220/803* (2013.01); *A63B 2220/836* (2013.01); *A63B 2225/50* (2013.01); *A63B 2230/06* (2013.01); *A63B 2230/75* (2013.01)

(56) References Cited

U.S. PATENT DOCUMENTS

| | | | |
|---|---|---|---|
| 9,521,962 B2 | 12/2016 | Leboeuf | |
| 9,724,023 B2 | 8/2017 | Swenson | |
| 9,788,785 B2 | 10/2017 | Leboeuf | |
| 10,307,066 B2 | 6/2019 | Jeon et al. | |
| 2003/0208133 A1* | 11/2003 | Mault .................... | A61B 5/087 600/531 |
| 2009/0018405 A1 | 1/2009 | Katsumura et al. | |
| 2013/0150746 A1* | 6/2013 | Tao ...................... | A61B 5/0833 600/531 |
| 2014/0074407 A1 | 3/2014 | Hernandez-Silveira et al. | |
| 2014/0128690 A1 | 5/2014 | Leboeuf | |
| 2014/0128691 A1 | 5/2014 | Olivier | |
| 2015/0289790 A1* | 10/2015 | Swenson ............ | A61B 5/14517 600/344 |
| 2015/0359458 A1 | 12/2015 | Erickson et al. | |
| 2016/0051156 A1* | 2/2016 | Kim ...................... | A61B 5/4866 600/513 |
| 2016/0166156 A1* | 6/2016 | Yuen ...................... | A61B 5/112 340/573.1 |
| 2016/0235309 A1 | 8/2016 | Olivier | |
| 2016/0328991 A1* | 11/2016 | Simpson ............ | G09B 19/0092 |
| 2016/0331274 A1 | 11/2016 | Leboeuf | |
| 2016/0337843 A1* | 11/2016 | Repka ...................... | H04W 8/22 |
| 2017/0079582 A1 | 3/2017 | Leboeuf | |
| 2018/0001174 A1 | 1/2018 | Aoshima et al. | |
| 2018/0055375 A1 | 3/2018 | Martinez et al. | |
| 2018/0055439 A1 | 3/2018 | Pham et al. | |
| 2018/0235480 A1 | 8/2018 | Olivier | |
| 2018/0249951 A1 | 9/2018 | Bonomi et al. | |

FOREIGN PATENT DOCUMENTS

| | | |
|---|---|---|
| KR | 10-2013-0016052 A | 2/2013 |
| KR | 10-2015-0110412 A | 10/2015 |
| KR | 10-2016-0007889 A | 1/2016 |

OTHER PUBLICATIONS

Extended European Search Report dated Aug. 28, 2019, issued in a counterpart European application No. 19166612.2-1126.
Korean Office Action with English translation dated Sep. 26, 2022; Korean Appln. No. 10-2018-0037903.

* cited by examiner

ELECTRONIC DEVICE FOR PROVIDING INFORMATION REGARDING EXERCISE STATE BASED ON METABOLITE INFORMATION AND METHOD THEREOF

CROSS-REFERENCE TO RELATED APPLICATION(S)

This application is based on and claims priority under 35 U.S.C. § 119 of a Korean patent application number 10-2018-0037903, filed on Apr. 2, 2018, in the Korean Intellectual Property Office, the disclosure of which is incorporated by reference herein its entirety.

BACKGROUND

1. Field

The disclosure relates to an electronic device for providing information regarding an exercise state and a method thereof.

2. Description of Related Art

As portable electronic devices such as smartphones or wearable devices have come into wide use, technologies for monitoring a user's exercise state using an electronic device and providing an appropriate service for the user have been increased. For example, an electronic device may measure calories (or energy) consumed while a user does exercise, and may inform the user of the measured calorie consumption. The electronic device may provide an environment in which the user is capable of consistently doing exercise, by a method of informing the user of calorie consumption and exercise efficiency.

The above information is presented as background information only to assist with an understanding of the disclosure. No determination has been made, and no assertion is made, as to whether any of the above might be applicable as prior art with regard to the disclosure.

SUMMARY

Aspects of the disclosure are to address at least the above-mentioned problems and/or disadvantages and to provide at least the advantages described below. Accordingly, an aspect of the disclosure is to provide an electronic device that measures a metabolite or a heart rate of a user without using separate large equipment, thereby measuring not only calorie consumption but also energy sources used to consume calories.

A method for measuring calorie consumption may include, for example, a method based on respiratory gas analysis and a method based on statistics. The method based on respiratory gas analysis may refer to a method of measuring calorie consumption using oxygen and carbon dioxide contained in respiratory gas of a user. Because the amount of oxygen required for oxidation of fat molecules differs from the amount of oxygen required for oxidation of carbohydrate molecules, not only calorie consumption but also energy sources (carbohydrate, protein, and fat) used to consume calories may be measured using respiratory gas. However, to analyze the user's respiratory gas, an electronic device has to be equipped with a nose clip and separate large equipment for gas capture, and therefore the portability of the electronic device and user convenience may be degraded.

In the case of using the method based on statistics, an electronic device may store, in a memory, statistical information about calorie consumption previously measured according to the type of exercise and exercise time. The electronic device, when receiving a user input for selecting exercise time, the type of exercise, age, or weight, may calculate calorie consumption of a user through the stored statistical information and the information according to the user input. In the case of the method based on statistics, the electronic device does not need to be equipped with separate measurement equipment, but may not measure energy sources used to consume calories. For example, in a case where the user does an exercise aimed at burning off fat, such as an aerobic exercise, the user may inefficiently repeat the exercise without knowing a fat burning zone if the electronic device cannot detect whether fat is burned off.

Aspects of the disclosure are to address at least the above-mentioned problems and/or disadvantages and to provide at least the advantages described below.

Additional aspects will be set forth in part in the description which follows and, in part, will be apparent from the description, or may be learned by practice of the presented embodiments.

In accordance with an aspect of the disclosure, an electronic device is provided. The electronic device includes a first sensor module, a second sensor module, at least one output device, and at least one processor. The at least one processor is configured to detect an event relating to start of an exercise state, obtain motion information corresponding to the exercise state using the first sensor module, obtain metabolite information of a user using the second sensor module, and provide information regarding the exercise state to the user through the at least one output device, based on whether the metabolite information satisfies a specified condition.

In accordance with another aspect of the disclosure, a method of an electronic device is provided. The method includes detecting an event relating to a start of an exercise state, obtaining motion information corresponding to the exercise state, obtaining metabolite information of a user, determining whether the metabolite information satisfies a specified condition, and providing information regarding the exercise state to the user, based on whether the metabolite information satisfies the specified condition.

In accordance with another aspect of the disclosure, an electronic device is provided. The electronic device includes a memory and at least one processor coupled to the memory. The at least one processor is configured to detect an event relating to start of an exercise state, obtain motion information corresponding to the exercise state, obtain metabolite information of a user, and provide information regarding the exercise state to the user, based on whether the metabolite information satisfies a specified condition.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

Throughout the drawings, like reference numerals will be understood to refer to like parts, components, and structures.

DETAILED DESCRIPTION

Hereinafter, various embodiments of the disclosure will be described with reference to accompanying drawings. However, those of ordinary skill in the art will recognize that various modifications, equivalents, and/or alternatives can be made to the various embodiments described herein without departing from the scope and spirit of the disclosure.

Figure 1:
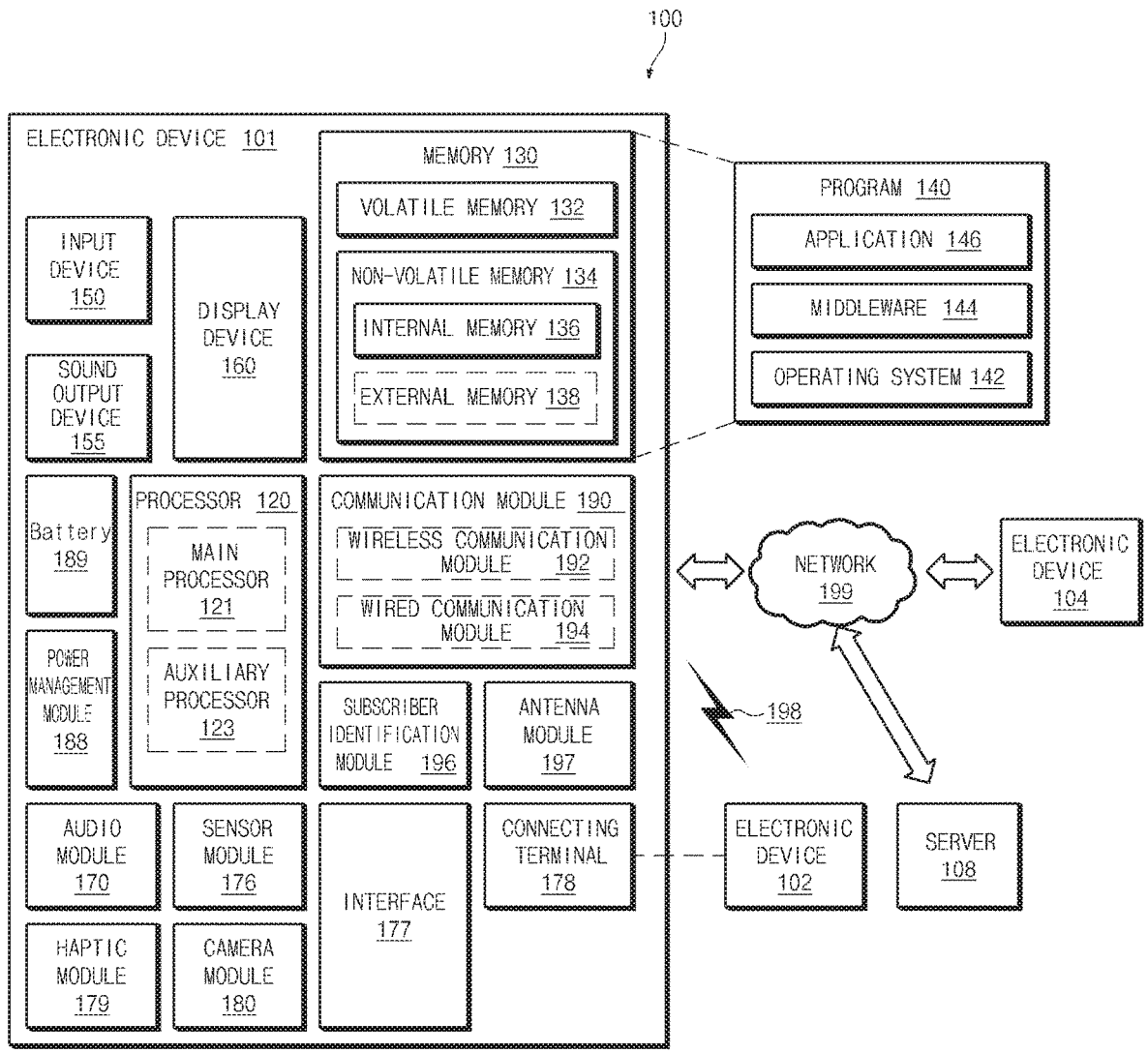
FIG. 1 is a block diagram illustrating an electronic device in a network environment according to various embodiments of the disclosure.

FIG. 1 is a block diagram illustrating an electronic device 101 in a network environment 100 according to various embodiments.

Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing record, and the receiver may be used for incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., PCB). According to an embodiment, the antenna module 197 may include a plurality of antennas. In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Figure 2:
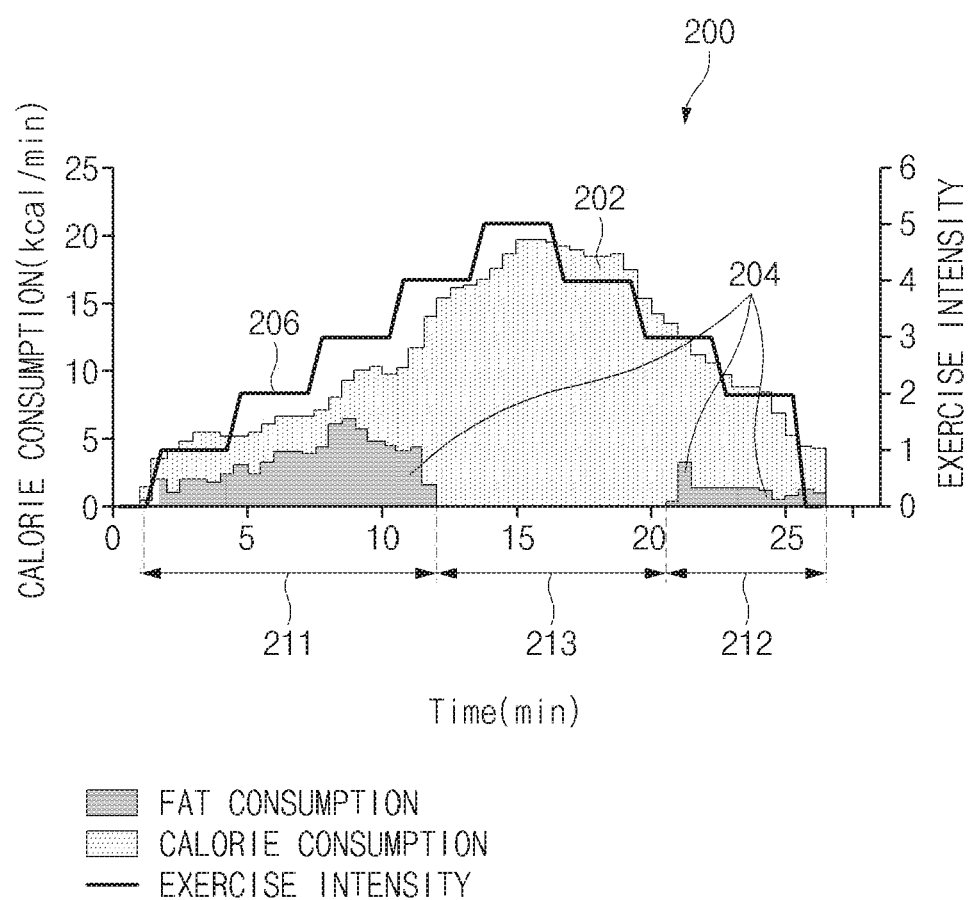
FIG. 2 is a graph depicting calorie consumption and fat burning zones depending on an exercise state according to various embodiments of the disclosure.

FIG. 2 is a graph 200 depicting calorie consumption and fat burning zones depending on an exercise state according to various embodiments of the disclosure. The graph 200 illustrated in FIG. 2 is merely illustrative, and the relationship between the exercise state, the calorie consumption, and the fat burning zones included in the graph 200 is not limited to the example illustrated in FIG. 2.

Referring to FIG. 2, the horizontal axis of the graph 200 may represent time (unit: minute). The vertical axis of the graph 200 may represent calorie consumption or fat consumption (unit: kcal/min) and exercise intensity according to various embodiments of the disclosure. Although FIG. 2 illustrates exercise intensity as an example, the graph 200 may represent a different exercise state other than the exercise intensity. The exercise state may include at least one of, for example, exercise intensity, the type of exercise, exercise speed, and exercise time.

According to an embodiment, the graph 200 may include first data 202 representing a variation in calorie consumption over time, second data 204 representing a variation in fat consumption over time, and third data 206 representing a variation in exercise intensity over time. According to an embodiment, the graph 200 may include data representing a variation in exercise speed over time other than the exercise intensity.

According to an embodiment, a user of the electronic device 101 may consume calories while doing exercise. The electronic device 101 may measure the calorie consumption, based on previously stored user information (e.g., age, weight, or gender) and an exercise state measured during the user's exercise. Alternatively, the electronic device 101 may measure the calorie consumption, based on user information and the user's heart rate information measured during the user's exercise.

According to an embodiment, the calorie consumption may vary depending on time and an exercise state. For example, as represented by the first data 202 and the third data 206, the calorie consumption may increase with an increase in the user's exercise intensity and may decrease with a decrease in the user's exercise intensity. Energy sources that consume the user's calories may include, for example, carbohydrate, protein, and fat. The percentages of the energy sources used when calories are consumed may vary depending on time and an exercise state. For example, as represented by the second data 204, fat may be burned off in a first zone 211 and a second zone 212 while calories are consumed, but may not be burned off in a third zone 213 while calories are consumed.

In the following embodiments, the electronic device 101 may detect the first zone 211 and the second zone 212 in which fat is burned off (or consumed) while the user does exercise, through the user's metabolite information or the user's heart rate information, thereby providing information regarding the user's exercise state. For example, the electronic device 101 may determine, in real time, whether fat is burned off while the user does exercise and may guide a way for the user to exercise, based on whether fat is burned off. In this case, the electronic device 101 may lead the user to maintain an exercise state (e.g., exercise intensity, the type of exercise, or exercise speed) that corresponds to a zone in which fat is burned off. In another example, the electronic device 101 may measure an exercise state, calorie consumption, and fat consumption from start to finish of the user's exercise and may store the measured data (e.g., the first data 202, the second data 204, and the third data 206 in the graph 200). The electronic device 101 may recommend an appropriate way for the user to exercise, based on the stored data.

Figure 3:
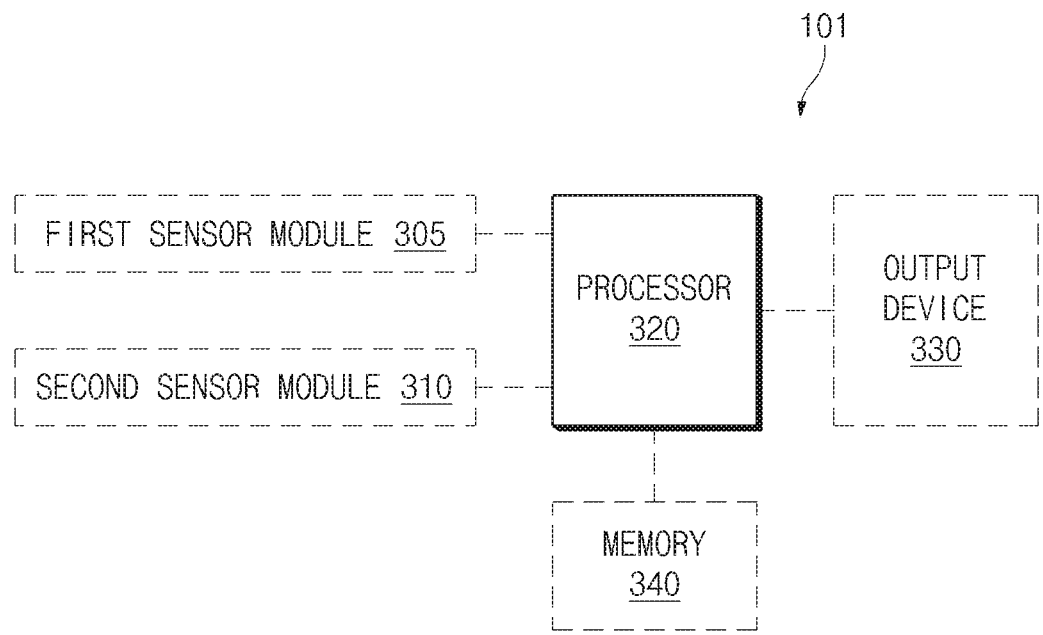
FIG. 3 is a block diagram illustrating the electronic device for determining a fat burning zone according to various embodiments of the disclosure.

FIG. 3 is a block diagram illustrating the electronic device 101 for determining a fat burning zone according to various embodiments of the disclosure.

Referring to FIG. 3, the electronic device 101 may include a first sensor module 305 (e.g., a first sensor), a second sensor module 310 (e.g., a second sensor), a processor 320 (e.g., the processor 120 of FIG. 1), at least one output device 330, and a memory 340 (e.g., the memory 130 of FIG. 1). According to an embodiment, the electronic device 101 may omit at least one of the first sensor module 305, the second sensor module 310, the at least one output device 330, and the memory 340.

According to an embodiment, the first sensor module 305 may sense a movement of the electronic device 101. The first sensor module 305 may include a motion sensor, which may be, for example, an acceleration sensor, a gyro sensor, a geo-magnetic sensor, or an atmospheric pressure sensor. The first sensor module 305 may sense the movement of the electronic device 101 by obtaining a signal generated by the movement of the electronic device 101 and transferring the obtained signal to the processor 320. The electronic device 101 may identify a user's exercise state corresponding to the movement of the electronic device 101 by detecting the movement of the electronic device 101 through the first sensor module 305.

According to an embodiment, the electronic device 101 may omit the first sensor module 305. For example, an external electronic device (e.g., the electronic device 102 or the electronic device 104 of FIG. 1) in communication with the electronic device 101 may identify the user's exercise state through a sensor module that performs a function corresponding to the first sensor module 305. The electronic device 101 may identify the exercise state by receiving motion information corresponding to the exercise state from the external electronic device. In this case, the external electronic device may refer to a wearable device, a medical appliance, a smartphone, a tablet PC, a nearable device, or a patch that is worn on the user's body, and the electronic device 101 may refer to a smartphone, a tablet PC, or a wearable device that is distinct from the external electronic device.

According to an embodiment, the second sensor module 310 may sense a metabolite of the user. The second sensor module 310 may include at least one of, for example, a colorimetric sensor, a semiconductor sensor, and an enzyme sensor that are configured to sense a metabolite. The metabolite may include, for example, lactate or a ketone body. According to an embodiment, anaerobic respiration may occur due to lack of oxygen caused by power exercise of the user. When the anaerobic respiration occurs, lactate may be produced in the user's body. The lactate may suppress fat consumption. Therefore, when a lactate value (e.g., a lactate concentration) increases, fat consumption may decrease. According to an embodiment, when fat breaks down, a fatty acid (3-lipatic acid) may be produced. The fatty acid may be separated as a diose by a β-oxidation process in mitochondria. While the fatty acid is separated as the diose, a ketone body may be produced. Therefore, when fat consumption increases, a ketone body value (e.g., a ketone body concentration) may increase. The electronic device 101 may determine whether fat is burned off in the user's body, by measuring a lactate value or a ketone body value through the second sensor module 310.

According to an embodiment, the electronic device 101 may omit the second sensor module 310 on the same principle as that applied to the first sensor module 305. For example, the electronic device 101 may identify the user's metabolite by receiving metabolite information from the external electronic device.

According to an embodiment of the disclosure, the at least one output device 330 may include the display device 160, the sound output device 155, or the haptic module 179 of FIG. 1. The at least one output device 330 may output information regarding an exercise state. For example, the electronic device 101 may display the user's exercise state at the time when fat is burned off, or may display a user interface (UI) for guiding a way for the user to exercise, through the display device 160 (e.g., a display). In another example, the electronic device 101 may output a sound through the sound output device 155 (e.g., a speaker) to inform of the time when the user's fat is burned off or the time when the user's fat is not burned off. In yet another example, the electronic device 101 may output a vibration at least once through the haptic module 179 to inform of the time when the user's fat is burned off or the time when the user's fat is not burned off.

According to an embodiment, the electronic device 101 may omit the at least one output device 330. For example, the electronic device 101 may transmit information regarding an exercise state to the external electronic device in communication with the electronic device 101 to provide the information regarding the exercise state to the user through the external electronic device. In this case, the external electronic device may refer to a wearable device or an accessory device (e.g., earphones or a headset) that is worn on the user's body, and the electronic device 101 may refer to a smartphone or a wearable device that is distinct from the external electronic device.

According to an embodiment, the processor 320 may be operatively coupled with the first sensor module 305, the second sensor module 310, the at least one output device 330, and the memory 340 to perform an overall function of the electronic device 101. The processor 320 may be constituted by one or more processors and may be physically divided into and separately driven as a main processor (e.g., the main processor 121 of FIG. 1) that performs high-performance processing and an auxiliary processor (e.g., the auxiliary processor 123) that performs low-power processing. For example, the first sensor module 305 or the second sensor module 310 may be coupled to the auxiliary processor while the main processor operates in an idle mode. According to situations, one processor may perform processing while switching between high performance and low power. The processor 320 may include, for example, an application processor (AP).

According to an embodiment, the processor 320 may detect an event relating to start of an exercise state. For example, the processor 320 may detect the event by detecting a movement of the electronic device 101 through the first sensor module 305 or receiving a user input representing the start of the exercise state.

According to an embodiment, the processor 320 may obtain motion information corresponding to the exercise state using the first sensor module 305 and may obtain the user's metabolite information using the second sensor module 310. In another example, the processor 320 may receive the motion information or the metabolite information from the external electronic device.

According to an embodiment, the processor 320 may determine whether the metabolite information satisfies a specified condition. The specified condition may mean whether the user's exercise state satisfies a fat burning zone. For example, when a lactate value is lower than a specified threshold value or a ketone body value is higher than or equal to another specified threshold value, the processor 320 may determine that the user's fat is burned off.

According to an embodiment, the processor 320 may provide information regarding the exercise state through the at least one output device 330. The information regarding the exercise state may represent, for example, whether fat is burned off in the currently measured exercise state. The processor 320 may display whether the user's fat is burned off, through the at least one output device 330 in real time. In another example, the information regarding the exercise state may represent at least one of the type of exercise, exercise intensity, exercise speed, and exercise time when fat is burned off. After the user's exercise is completed, the processor 320 may recommend an appropriate way for the user to exercise, based on the measured data. The appropriate way for the user to exercise may refer to, for example, an exercise state when fat is burned off. According to an embodiment, the processor 320 may provide the information regarding the exercise state to the user through the external electronic device.

According to an embodiment, the memory 340 may store instructions used by the processor 320 to perform operations of the electronic device 101. According to an embodiment, the memory 340 may store information regarding at least one of calorie consumption, fat consumption, and an exercise state.

According to an embodiment, the electronic device 101 may further include communication circuitry (e.g., the communication module 190 of FIG. 1) for performing communication with the external electronic device. The communication circuitry may perform communication with the external electronic device coupled with the electronic device 101 under the control of the processor 320.

According to an embodiment, the electronic device 101 may further include a photoplethysmogram (PPG) sensor for measuring the user's heart rate. For example, when a heart rate measured during the user's exercise corresponds to a predetermined percentage (e.g., 60% to 70%) of the user's maximum heart rate, the electronic device 101 may determine that fat is burned off. The electronic device 101 may determine whether the user's fat is burned off, by using heart rate information instead of metabolite information, or may raise the accuracy of measurement of a fat burning zone, by using both the metabolite information and the heart rate information.

Figure 4:
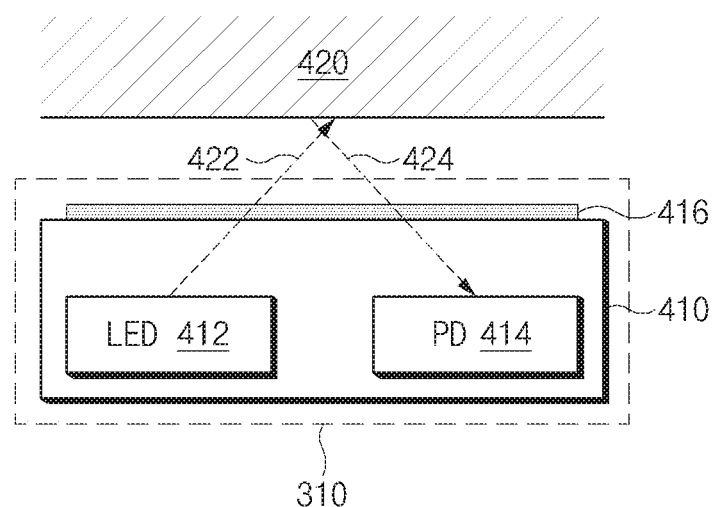
FIG. 4 is a block diagram illustrating a colorimetric sensor for measuring a metabolite according to various embodiments of the disclosure.

FIG. 4 is a block diagram illustrating a colorimetric sensor for measuring a metabolite according to various embodiments.

Referring to FIG. 4, the second sensor module 310 may refer to a colorimetric sensor that is constituted by a PPG sensor 410 and a coating material 416 in a film form. The PPG sensor 410 may include at least one light emitting diode (LED) 412 and at least one photodiode (PD) 414. The at least one LED 412 may convert electrical energy to light energy. The at least one PD 414 may convert light energy to electrical energy.

According to an embodiment, light 422 generated from the LED 412 may have at least one wavelength. At least part of the light 422 may be absorbed into or reflected by an object 420 (e.g., a user's body). The absorbance of lactate or a ketone body may vary depending on a concentration, and therefore the PD 414 may measure a lactate value or a ketone body value (or concentration) in the user's body by sensing light 424 reflected from the object 420.

According to an embodiment, the second sensor module 310 may include the coating material 416 to sense light with a wavelength that corresponds to lactate or a ketone body. According to an embodiment, the coating material 416 may be disposed on an upper end of the PPG sensor 410. The electronic device 101 may measure a metabolite using the coating material 416 in a film form that is disposed on the upper end of the PPG sensor 410. Accordingly, the electronic device 101 may improve user convenience and portability without separate equipment mounted therein.

Figure 5:
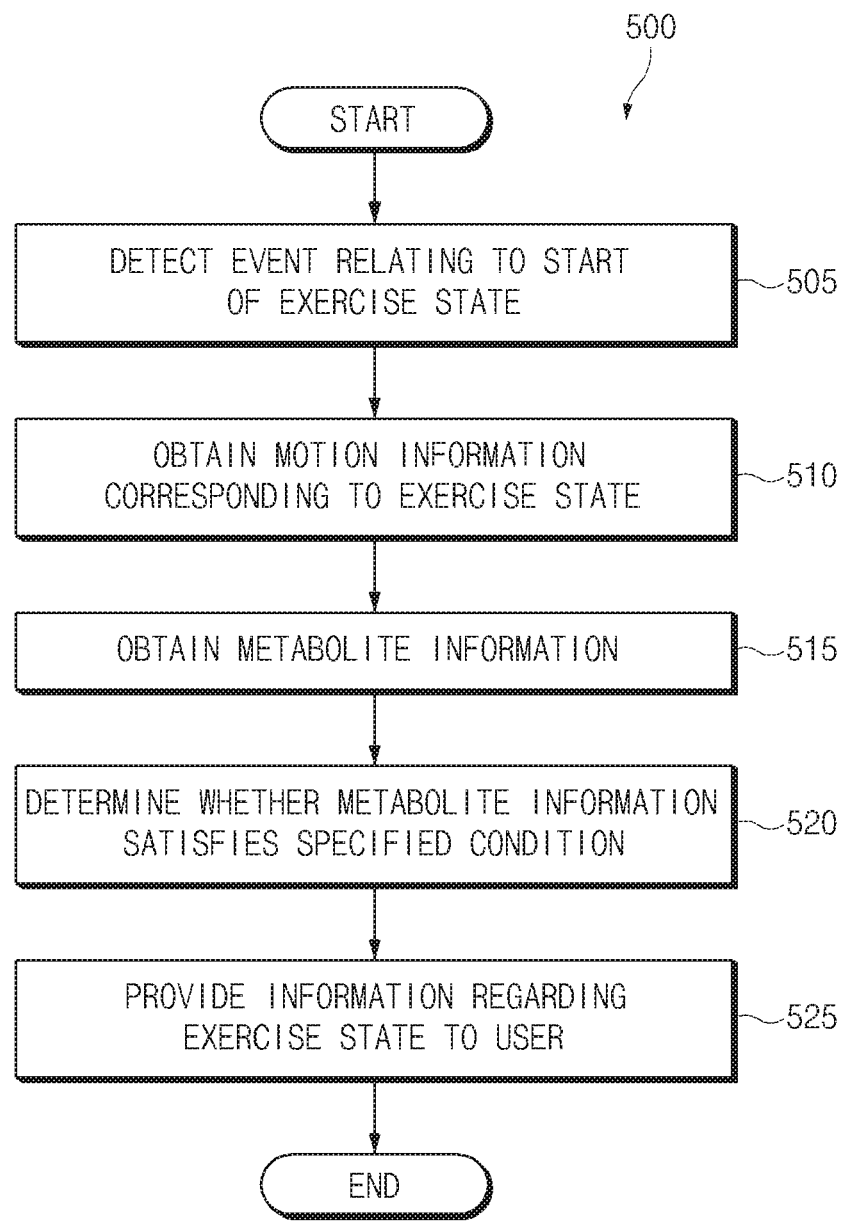
FIG. 5 is a flowchart illustrating an operation of providing information regarding an exercise state based on metabolite information, by the electronic device, according to various embodiments of the disclosure.

FIG. 5 is a flowchart illustrating an operation of providing information regarding an exercise state based on metabolite information, by the electronic device 101, according to various embodiments of the disclosure. Operations illustrated in FIG. 5 may be performed by the electronic device 101 or components (e.g., the processor 320) included in the electronic device 101.

Referring to FIG. 5, in operation 505 of a method 500, the electronic device 101 (e.g., the processor 320) may detect an event relating to start of an exercise state. According to an embodiment, the electronic device 101 may determine whether a user starts to do exercise, by using the first sensor module 305. In this case, the electronic device 101 may obtain at least one piece of first data relating to a movement of the electronic device 101 that corresponds to the user's motion, through the first sensor module 305 (e.g., an acceleration sensor). For example, the electronic device 101 may obtain the first data, based on a specified period. The electronic device 101 may obtain a reference value by removing noise included in the first data. For example, the electronic device 101 may obtain the reference value using a low pass filter (LPF) or an average filter (AV). The electronic device 101 may previously store the reference value in the memory 340. The electronic device 101 may obtain at least one piece of second data relating to the movement of the electronic device 101 through the first sensor module 305. The electronic device 101 may remove noise from the second data and may determine the difference between the reference value stored in the memory 340 and the second data from which the noise is removed. The electronic device 101 may determine whether the user starts to do exercise, based on the magnitude or regularity of the determined difference.

In another example, the electronic device 101 may receive a user input for determining the start of the exercise state. The user input may include, for example, a touch input for selecting an input button displayed on the display of the electronic device 101 or a voice input of the user. In another example, when an application for managing the user's exercise state is executed, the electronic device 101 may determine that the user starts to do exercise.

In operation 510, the electronic device 101 may obtain motion information corresponding to the exercise state. The motion information may include, for example, exercise time, exercise speed, exercise intensity, or the type of exercise. According to an embodiment, the electronic device 101 may obtain the motion information through the first sensor module 305, or may receive the motion information from an external electronic device. According to another embodiment, the electronic device 101 may obtain the motion information, based on a user input for entering exercise time, exercise speed, exercise intensity, or the type of exercise.

In operation 515, the electronic device 101 may obtain metabolite information. The metabolite information may include, for example, a lactate value or a ketone body value. According to an embodiment, the electronic device 101 may obtain the metabolite information through the second sensor module 310, or may receive the metabolite information from the external electronic device. Although FIG. 5 illustrates the method 500 of the electronic device 101 that sequentially performs operation 510 and operation 515, the sequence in which operation 510 and operation 515 are executed is not limited to the example illustrated in FIG. 5. For example, the electronic device 101 may preferentially obtain the metabolite information. In another example, the electronic device 101 may simultaneously obtain the motion information and the metabolite information.

In operation 520, the electronic device 101 may determine whether the metabolite information satisfies a specified condition. According to an embodiment, the electronic device 101 may determine whether the user's fat is burned off, based on the obtained lactate value or the obtained ketone body value. For example, the concentration of a ketone body may increase with an increase in fat consumption. Therefore, when the concentration of the ketone body is higher than or equal to a specified threshold value (e.g., 0 to 10+mM), the electronic device 101 may determine that the metabolite information satisfies the specified condition. In another example, lactate suppresses consumption of fat, and therefore when the concentration of lactate is lower than another specified threshold value, the electronic device 101 may determine that the metabolite information satisfies the specified condition.

In operation 525, the electronic device 101 may provide information regarding the exercise state to the user, based on whether the metabolite information satisfies the specified condition. For example, the electronic device 101 may display whether fat is burned off during the user's exercise, to the user in real time through the at least one output device 330. In another example, the electronic device 101 may measure the exercise state, calorie consumption over time, and fat consumption over time from start to finish of the user's exercise and may recommend an appropriate way for the user to exercise, based on the measured data after the completion of the exercise. The appropriate way for the user to exercise may refer to, for example, an exercise state when fat is burned off.

Figure 6:
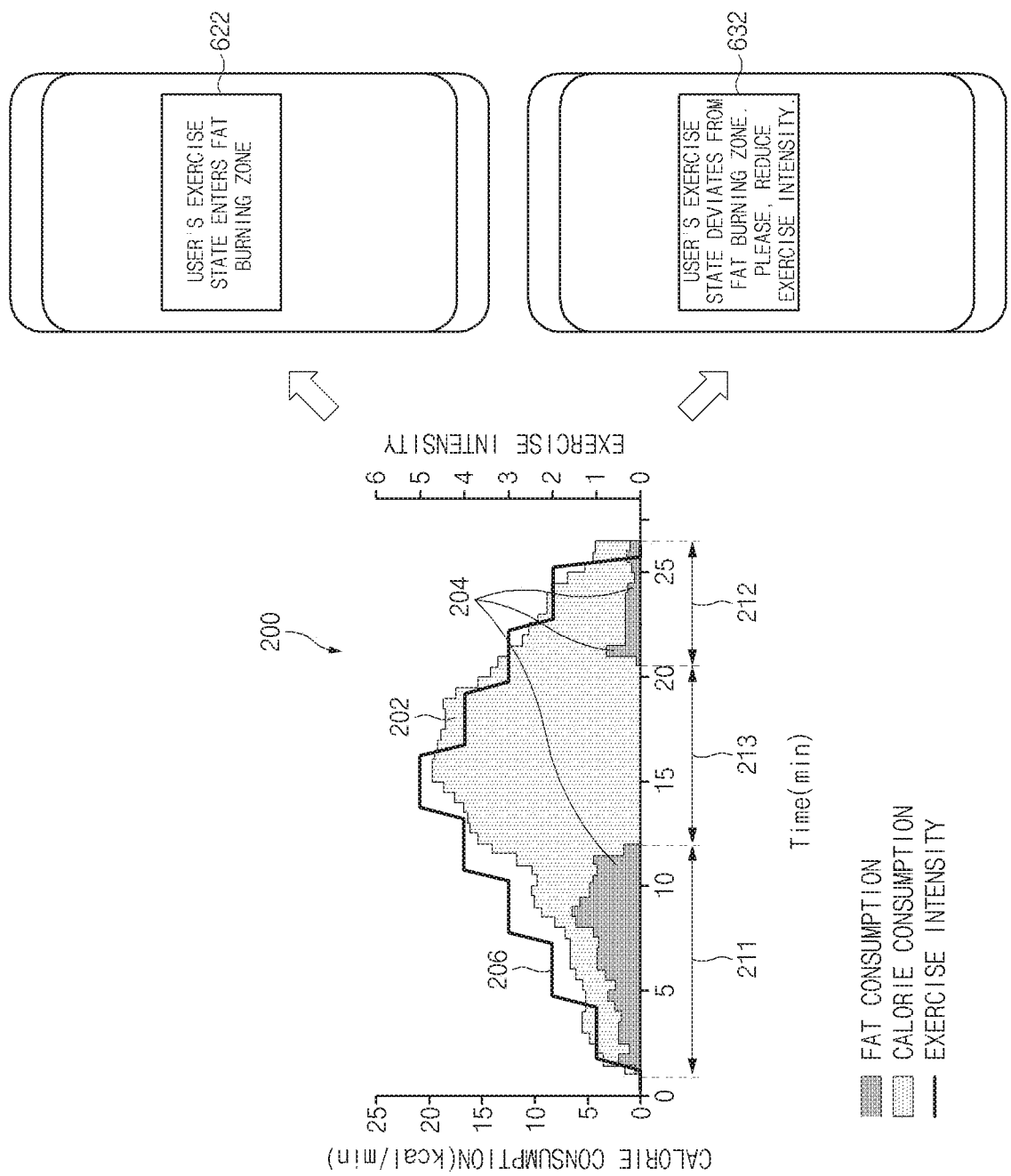
FIG. 6 is a view illustrating a user interface representing that fat is burned off, based on metabolite information according to various embodiments of the disclosure.

FIG. 6 is a view illustrating a user interface representing that fat is burned off, based on metabolite information according to various embodiments of the disclosure.

Referring to FIG. 6, as represented by the first data 202 and the third data 206 in the graph 200, calories may be consumed according to time and an exercise state (e.g., exercise intensity) while a user does exercise. As represented by the second data 204, a percentage of calorie consumption may correspond to fat consumption. For example, fat may be burned off in the first zone 211 and the second zone 212 while calories are consumed, but may not be burned off in the third zone 213 even while calories are consumed.

According to an embodiment, the electronic device 101 may inform, in real time, the user whether fat is burned off during the user's exercise, based on metabolite information. For example, when the user's exercise state enters the first zone 211 or the second zone 212 in which fat is burned off, the electronic device 101 may display a UI 622 representing that the user's exercise state enters the fat burning zone, through the display. Although FIG. 6 illustrates an example that the UI 622 is displayed through the display, the electronic device 101 may output a sound or vibration for informing the user that the user's exercise state enters the fat burning zone. In another example, the electronic device 101 may provide a UI representing that the user's exercise state enters the fat burning zone, through an external electronic device (e.g., a wearable device, earphones, or a headset).

According to an embodiment, when the user's exercise state enters the third zone 213 in which fat is not burned off, the electronic device 101 may display, through the display, a UI 632 representing that the user's exercise state deviates from the fat burning zone, or may output a sound or vibration.

According to an embodiment, the electronic device 101 may guide a way for the user to exercise, based on metabolite information and motion information to allow the user to maintain an exercise state corresponding to a zone in which fat is burned off. For example, when the user's exercise state enters a fat burning zone (e.g., the first zone 211 or the second zone 212), the electronic device 101 may provide a UI for recommending maintaining the current exercise state (e.g., exercise intensity of 0 to 3) to the user. In another example, when the user's exercise state deviates from a fat burning zone (e.g., when the user's exercise state enters the third zone 213), the electronic device 101 may provide a UI for recommending changing the user's exercise state (e.g., exercise intensity).

Figure 7:
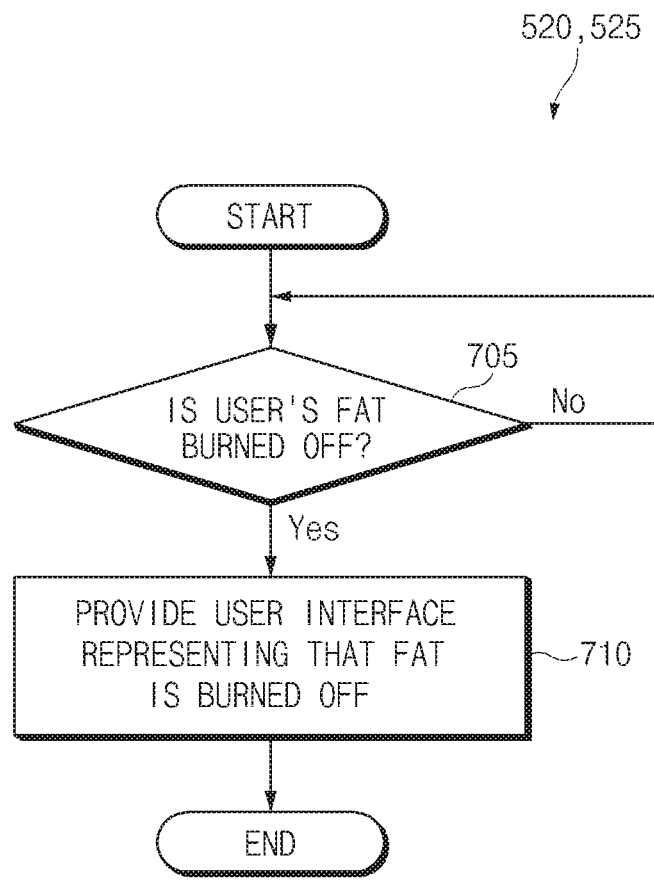
FIG. 7 is a flowchart illustrating an operation of providing a user interface representing that fat is burned off, by the electronic device, according to various embodiments of the disclosure.

FIG. 7 is a flowchart illustrating an operation of providing a user interface representing that fat is burned off, by the electronic device 101, according to various embodiments of the disclosure. Operations illustrated in FIG. 7 may refer to more specific operations of operations 520 and 525 in FIG. 5 according to various embodiments of the disclosure.

Referring to FIG. 7, in operation 705, the electronic device 101 (e.g., the processor 320) may determine whether a user's fat is burned off. For example, the electronic device 101 may obtain metabolite information such as lactate or a ketone body to determine whether the user's fat is burned off. When the user's fat is not burned off, the electronic device 101 may repeatedly perform operation 705.

When the user's fat is burned off, the electronic device 101 may, in operation 710, display the UI 622 representing that the user's fat is burned off, through the display. According to an embodiment, the electronic device 101 may inform the user that the user's fat is burned off, through a sound or vibration in addition to the screen displayed through the display.

Figure 8:
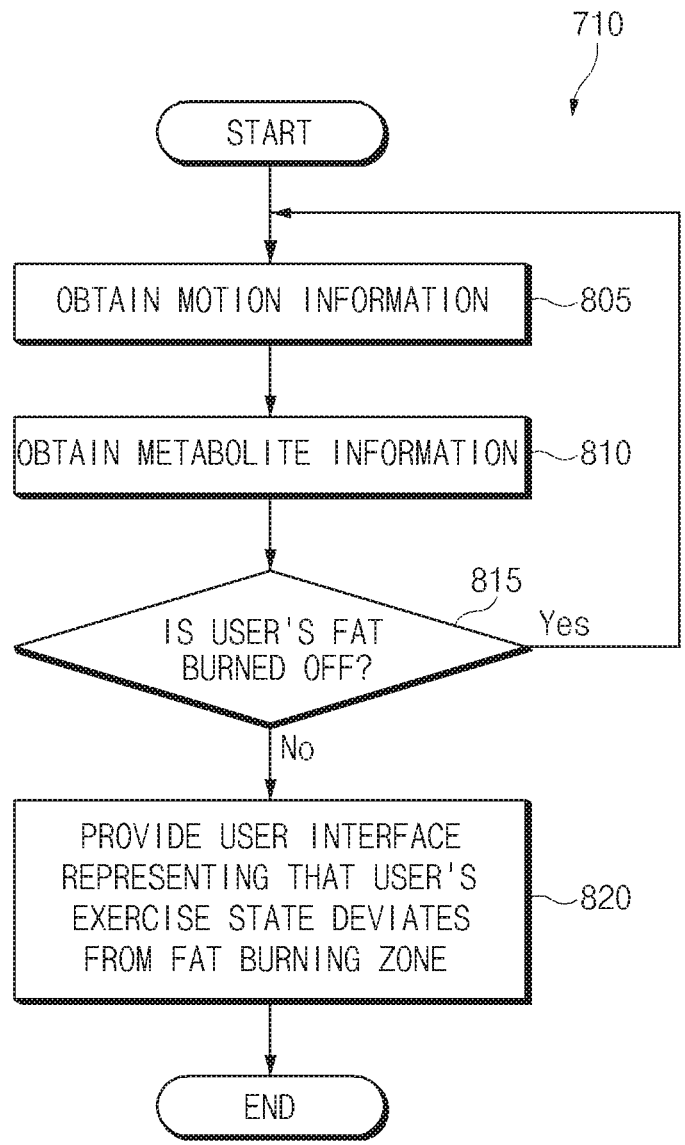
FIG. 8 is a flowchart illustrating an operation of providing a user interface representing that a user's exercise state deviates from a fat burning zone, by the electronic device, according to various embodiments of the disclosure.

FIG. 8 is a flowchart illustrating an operation of providing a user interface representing that a user's exercise state deviates from a fat burning zone, by the electronic device, according to various embodiments of the disclosure. Operations illustrated in FIG. 8 may refer to operations after operation 710 in FIG. 7.

Referring to FIG. 8, in operation 805, the electronic device 101 may obtain motion information. For example, the electronic device 101 may obtain the motion information through the first sensor module 305, or may receive the motion information from an external electronic device.

In operation 810, the electronic device 101 may obtain metabolite information. For example, the electronic device 101 may obtain the metabolite information through the second sensor module 310, or may receive the metabolite information from the external electronic device. According to an embodiment, the electronic device 101 may simultaneously perform operation 805 and operation 810, or may preferentially perform operation 810.

In operation 815, the electronic device 101 may determine whether the user's fat is burned off, based on the metabolite information. When the user's fat is burned off, the electronic device 101 may repeatedly perform operations 805, 810, and 815.

When the user's fat is not burned off, the electronic device 101 may, in operation 820, display the UI 632 representing that the user's exercise state deviates from a fat burning zone, through the display. According to an embodiment, the electronic device 101 may inform the user that the user's exercise state deviates from the fat burning zone, through a sound or vibration in addition to the screen displayed through the display. According to an embodiment, the electronic device 101 may guide an exercise state for entrance into a fat burning zone to the user, based on the metabolite information and the motion information. For example, when the user's fat is not burned off with an increase in the user's exercise intensity or exercise speed, the electronic device 101 may lead the user to reduce the exercise intensity or the exercise speed.

Figure 9:
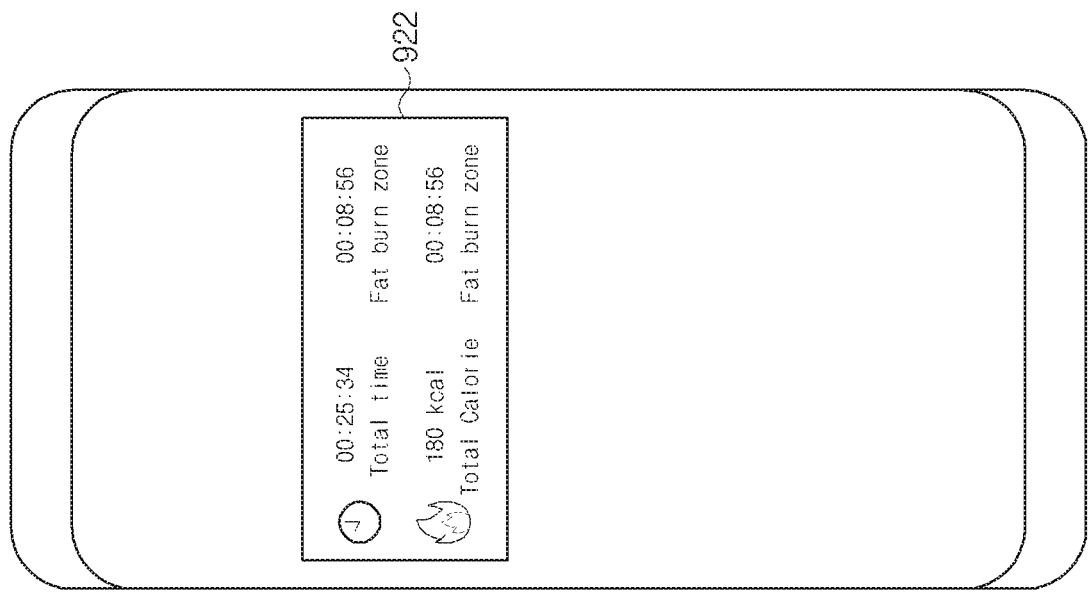
FIG. 9 is a view illustrating a user interface for guiding an appropriate way for a user to exercise according to various embodiments of the disclosure.
Figure 9:
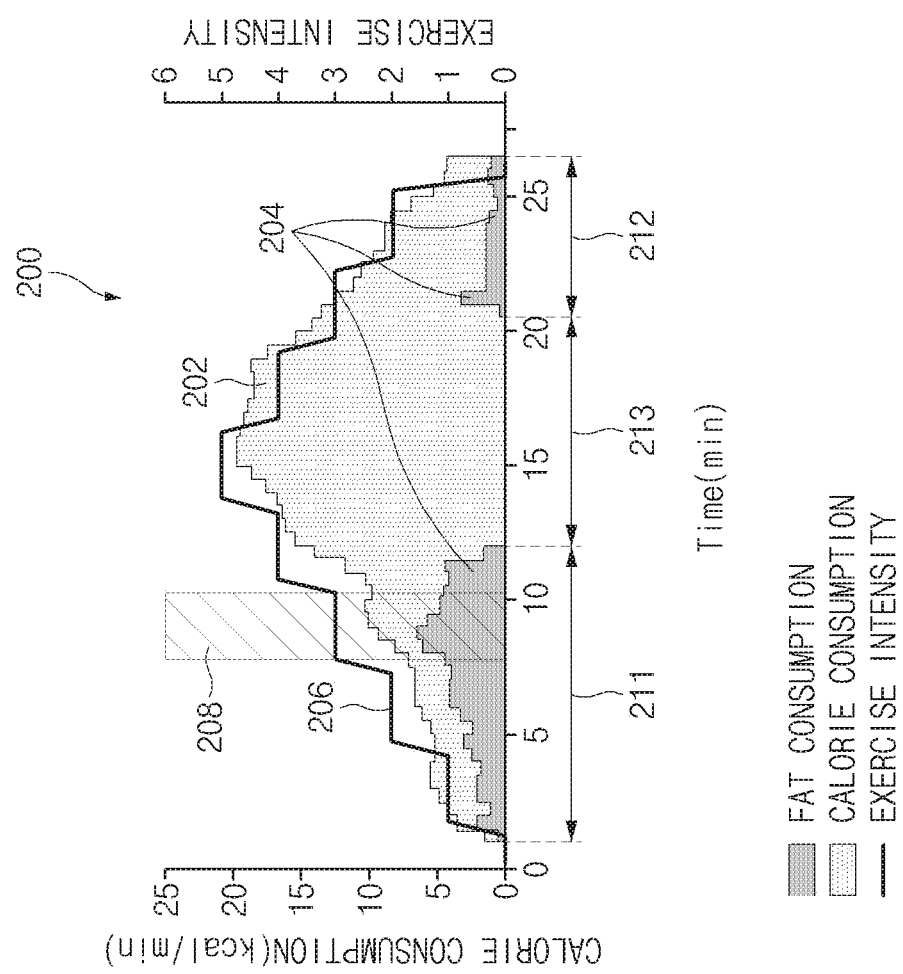

FIG. 9 is a view illustrating a user interface for guiding an appropriate way for a user to exercise according to various embodiments of the disclosure.

Referring to FIG. 9, the electronic device 101 may measure calorie consumption (e.g., the first data 202), fat consumption (e.g., the second data 204), and an exercise state variation (e.g., the third data 206) over time while the user does exercise. The electronic device 101 may store the measured data when the user's exercise is completed. For example, the electronic device 101 may store the measured data in the memory 340.

According to an embodiment, the electronic device 101 may display the graph 200 representing the measured data through the display to allow the user to recognize a fat burning zone. The electronic device 101 may display a zone in which fat is maximally burned off, through the display. For example, when the exercise intensity of the user of the electronic device 101 is 3 and the user's fat is maximally burned off for exercise time of 6 minutes to 10 minutes, the electronic device 101 may display a maximum fat burning zone 208 in the graph 200.

According to an embodiment, the electronic device 101 may display, through the display, a UI 922 representing the exercise state and the fat burning zone as numerical values, instead of the graph 200. The UI 922 may represent at least one of, for example, the type of exercise, average exercise speed, total exercise time, total calorie consumption, fat consumption, and a fat burning zone.

Figure 10:
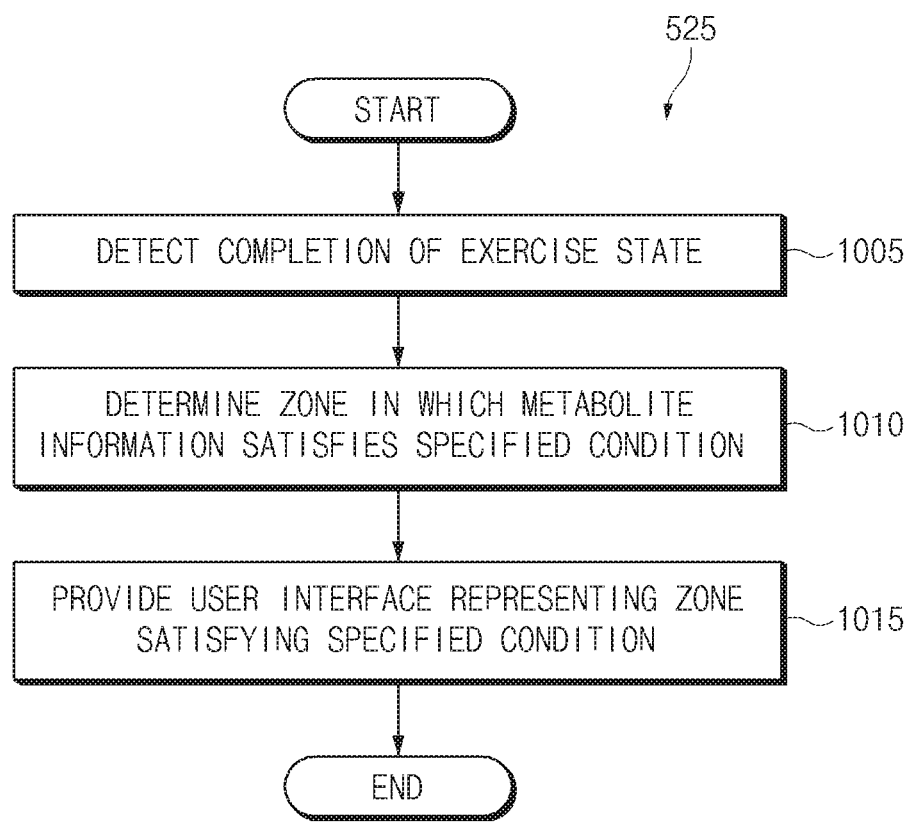
FIG. 10 is a flowchart illustrating an operation of guiding an appropriate way for a user to exercise, by the electronic device, according to various embodiments of the disclosure.

FIG. 10 is a flowchart illustrating an operation of guiding an appropriate way for a user to exercise, by the electronic device, according to various embodiments of the disclosure. Operations illustrated in FIG. 10 may refer to operations performed after operation 525 in FIG. 5.

Referring to FIG. 10, in operation 1005, the electronic device 101 may detect that the user's exercise state is completed. For example, when motion information is lower than a specified threshold value, the electronic device 101 may determine that the user's exercise state is completed. In another example, the electronic device 101 may receive a user input for completing the exercise state.

In operation 1010, the electronic device 101 may determine an exercise state zone (e.g., the first zone 211 or the second zone 212) in which metabolite information satisfies a specified condition. The exercise state zone may be represented by, for example, the type of exercise, exercise intensity, exercise speed, or exercise time. According to an embodiment, the electronic device 101 may determine a maximum fat burning zone in the exercise state zone that satisfies the specified condition.

In operation 1015, the electronic device 101 may provide a UI representing the determined exercise state zone to the user through the display. For example, the electronic device 101 may display the graph 200 including the fat burning zone, or may display the UI 922 representing the exercise state and the fat burning zone as numerical values.

Figure 11:
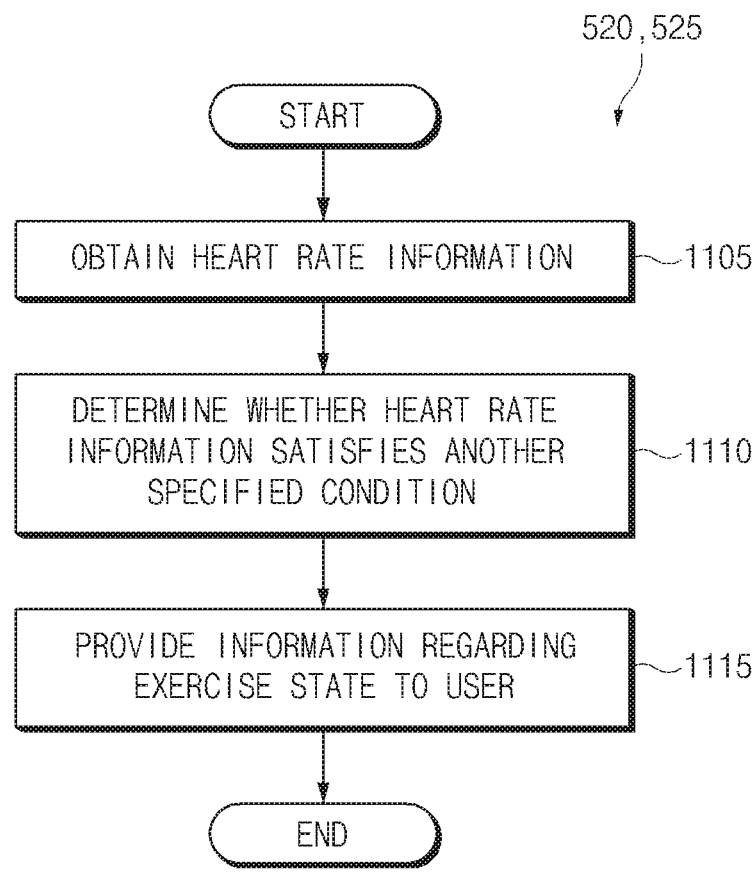
FIG. 11 is a flowchart illustrating an operation of providing information regarding an exercise state based on heart rate information, by the electronic device, according to various embodiments of the disclosure.

FIG. 11 is a flowchart illustrating an operation of providing information regarding an exercise state based on heart rate information, by the electronic device, according to various embodiments. Operations illustrated in FIG. 11 may be performed independently of the embodiments illustrated in FIGS. 5 to 10, or may be performed in operation 520 and operation 525 of FIG. 5.

According to an embodiment, the electronic device 101 may determine a fat burning zone using a user's heart rate information other than metabolite information. For example, the electronic device 101 may determine a percentage (e.g., 60% to 70%) of the user's maximum heart rate to be a fat burning zone.

Referring to FIG. 11, in operation 1105, the electronic device 101 may obtain the user's heart rate information according to various embodiments of the disclosure. For example, the electronic device 101 may obtain the heart rate information through a PPG sensor. In another example, the electronic device 101 may receive the heart rate information from an external electronic device in communication with the electronic device 101.

In operation 1110, the electronic device 101 may determine whether the heart rate information satisfies another specified condition. For example, when the obtained heart rate corresponds to 60% to 70% of the user's maximum heart rate, fat may be burned off, and therefore the electronic device 101 may determine that the heart rate information satisfies the other specified condition. According to an embodiment, the electronic device 101 may more accurately measure a fat burning zone by determining whether metabolite information satisfies a specified condition and whether the heart rate information satisfies the other specified condition.

In operation 1115, the electronic device 101 may provide information regarding an exercise state to the user through the at least one output device 330, based on whether the heart rate information satisfies the other specified condition. For example, the electronic device 101 may inform, in real time, the user whether the user's fat is burned off during the user's exercise. In another example, the electronic device 101 may measure the exercise state, calorie consumption over time, and fat consumption over time from start to finish of the user's exercise and may recommend an appropriate way for the user to exercise, based on the measured data after the completion of the exercise.

As described above, an electronic device (e.g., the electronic device 101 of FIG. 1) may include a first sensor module (e.g., the first sensor module 305 of FIG. 3), a second sensor module (e.g., the second sensor module 310 of FIG. 3), at least one output device (e.g., the output device 330 of FIG. 3), and a processor (e.g., the processor 320 of FIG. 3). The processor may be configured to detect an event relating to start of an exercise state, obtain motion information corresponding to the exercise state using the first sensor module, obtain metabolite information of a user using the second sensor module, and provide information regarding the exercise state to the user through the at least one output device, based on whether the metabolite information satisfies a specified condition.

According to an embodiment, the processor may be configured to detect the event by detecting a movement of the electronic device using the first sensor module or in response to a user input for starting the exercise state.

According to an embodiment, the second sensor module may include a colorimetric sensor, a semiconductor sensor, or an enzyme sensor, and the processor may be configured to obtain the metabolite information using the colorimetric sensor, the semiconductor sensor, or the enzyme sensor.

According to an embodiment, the second sensor module may include a colorimetric sensor, and the colorimetric sensor may include a PPG sensor (e.g., the PPG sensor 410 of FIG. 4) and a film (e.g., the coating material 416 of FIG. 4) disposed on an upper end of the PPG sensor.

According to an embodiment, the specified condition may include whether fat of the user is burned off, and the metabolite information may include a lactate value or a ketone body value. The processor may be configured to determine whether the user's fat is burned off, based on the lactate value or the ketone body value that is obtained using the colorimetric sensor.

According to an embodiment, the processor may be configured to provide a user interface (UI) representing that the user's fat is burned off, when the metabolite information satisfies the specified condition and provide a UI to make a request to change the exercise state, when the metabolite information does not satisfy the specified condition.

According to an embodiment, the processor may be configured to detect completion of the exercise state, determine a zone of the exercise state in which the metabolite information satisfies the specified condition, and provide a UI representing the zone of the exercise state through the at least one output device.

According to an embodiment, the electronic device may further include a third sensor module (e.g., a PPG sensor), and the processor may be configured to obtain heart rate information of the user using the third sensor module and provide the information regarding the exercise state to the user through the at least one output device, based on whether the heart rate information satisfies another specified condition.

As described above, a method (e.g., the method 500 of FIG. 5) of an electronic device may include detecting an event relating to start of an exercise state (e.g., operation 505 of FIG. 5), obtaining motion information corresponding to the exercise state (e.g., operation 510 of FIG. 5), obtaining metabolite information of a user (e.g., operation 515 of FIG. 5), determining whether the metabolite information satisfies a specified condition (e.g., operation 520 of FIG. 5), and providing information regarding the exercise state to the user, based on whether the metabolite information satisfies the specified condition (e.g., operation 525 of FIG. 5).

According to an embodiment, the detecting of the event may include detecting a movement of the electronic device or receiving a user input for starting the exercise state.

According to an embodiment, the obtaining of the metabolite information may include obtaining the metabolite information using a colorimetric sensor of the electronic device, and the colorimetric sensor may include a PPG sensor (e.g., the PPG sensor 410 of FIG. 4) and a film (e.g., the coating material 416 of FIG. 4) disposed on an upper end of the PPG sensor.

According to an embodiment, the specified condition may include whether fat of the user is burned off, and the metabolite information may include a lactate value or a ketone body value. The determining of whether the metabolite information satisfies the specified condition may include determining whether the user's fat is burned off, based on the lactate value or the ketone body value (e.g., operation 705 of FIG. 7).

According to an embodiment, the providing of the information regarding the exercise state to the user may include providing a UI representing that the user's fat is burned off, when the metabolite information satisfies the specified condition (e.g., operation 710 of FIG. 7) and providing a UI to make a request to change the exercise state, when the metabolite information does not satisfy the specified condition (e.g., operation 820 of FIG. 8).

According to an embodiment, the method may further include detecting completion of the exercise state (e.g., operation 1005 of FIG. 10), determining a zone of the exercise state in which the metabolite information satisfies the specified condition (e.g., operation 1010 of FIG. 10), and providing a UI representing the zone of the exercise state (e.g., operation 1015 of FIG. 10).

According to an embodiment, the method may further include obtaining heart rate information of the user (e.g., operation 1105 of FIG. 11) and determining whether the heart rate information satisfies another specified condition (e.g., operation 1110 of FIG. 10) according to various embodiments of the disclosure.

As described above, an electronic device (e.g., the electronic device 101 of FIG. 1) may include a processor (e.g., the processor 320 of FIG. 3). The processor may be configured to detect an event relating to start of an exercise state, obtain motion information corresponding to the exercise state, obtain metabolite information of a user, and provide information regarding the exercise state to the user, based on whether the metabolite information satisfies a specified condition.

According to an embodiment, the processor may be configured to obtain the motion information or the metabolite information from an external electronic device.

According to an embodiment, the processor may be configured to provide a UI representing that fat of the user is burned off, when the metabolite information satisfies the specified condition and provide a UI to make a request to change the exercise state, when the metabolite information does not satisfy the specified condition.

According to an embodiment, the processor may be configured to detect completion of the exercise state, determine a zone of the exercise state in which the metabolite information satisfies the specified condition, and provide a UI representing the zone of the exercise state.

According to an embodiment, the processor may be configured to obtain heart rate information of the user and provide the information regarding the exercise state to the user, based on whether the heart rate information satisfies another specified condition.

According to the embodiments of the disclosure, the electronic device determines a fat burning zone without separate large equipment, thereby providing user convenience and portability in a situation in which a user measures calorie consumption.

Furthermore, according to the embodiments of the disclosure, the electronic device determines a fat burning zone while a user does exercise, thereby providing an appropriate way for the user to exercise.

In addition, the disclosure may provide various effects that are directly or indirectly recognized.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

While the disclosure has been shown and described with reference to various embodiments thereof, it will be understood by those skilled in the art that various changes in form and details may be made therein without departing from the spirit and scope of the disclosure as defined by the appended claims and their equivalents.

An aspect of the disclosure is to provide an electronic device that measures a metabolite or a heart rate of a user without using separate large equipment, thereby measuring not only calorie consumption but also energy sources used to consume calories.

Another aspect of the disclosure is to provide an electronic device that guides an appropriate way for a user to exercise, based on a measured fat burning zone.

What is claimed is:
1. An electronic device comprising:
 a first sensor module;
 a second sensor module comprising a colorimetric sensor including a photoplethysmogram (PPG) sensor;
 at least one output device; and
 at least one processor configured to:
  detect an event relating to start of an exercise state,
  obtain, via the first sensor module, motion information corresponding to the exercise state,
  obtain, via the second sensor module, metabolite information of a user,
  determine in real time whether the metabolite information satisfies a specified condition, and
  provide information regarding whether the metabolite information satisfies the specified condition and at least one recommendation corresponding to whether the metabolite information satisfies the specified condition in real time,
 wherein the specified condition includes whether fat of the user is burned off,
 wherein the at least one processor is configured to:
  according to the metabolite information satisfying the specified condition, provide information indicating that the user's fat is being burned and a recommendation to maintain the exercise state, and
  according to the metabolite information not satisfying the specified condition, provide information indicating that the user's fat is not burning and a recommendation to change the exercise state, and
 wherein the PPG sensor comprises a film disposed on an upper end of the PPG sensor to sense light.

2. The electronic device of claim 1, wherein the at least one processor is further configured to detect the event by detecting a movement of the electronic device using the first sensor module or in response to a user input for starting the exercise state.

3. The electronic device of claim 1,
 wherein the second sensor module includes a colorimetric sensor, a semiconductor sensor, or an enzyme sensor, and
 wherein the at least one processor is further configured to obtain the metabolite information using the colorimetric sensor, the semiconductor sensor, or the enzyme sensor.

4. The electronic device of claim 1,
 wherein the specified condition includes whether fat of the user is burned off,
 wherein the metabolite information includes a lactate value or a ketone body value, and
 wherein the at least one processor is further configured to determine whether the user's fat is burned off, based on the lactate value or the ketone body value that is obtained using the colorimetric sensor.

5. The electronic device of claim 4, wherein the at least one processor is further configured to:
 provide a first user interface (UI) representing that the user's fat is burned off, when the metabolite information satisfies the specified condition; and
 provide a second UI to make a request to change the exercise state, when the metabolite information does not satisfy the specified condition.

6. The electronic device of claim 1, wherein the at least one processor is further configured to:
 detect a completion of the exercise state;
 determine a zone of the exercise state in which the metabolite information satisfies the specified condition; and
 provide a user interface (UI) representing the zone of the exercise state through the at least one output device.

7. The electronic device of claim 1, further comprising:
 a third sensor module,
 wherein the at least one processor is further configured to:
  obtain heart rate information of the user using the third sensor module, and
  provide the information regarding the exercise state to the user through the at least one output device, based on whether the heart rate information satisfies another specified condition.

8. A method of an electronic device, the method comprising:
- detecting an event relating to a start of an exercise state;
- obtaining, via a first sensor, motion information corresponding to the exercise state;
- obtaining, via a second sensor, metabolite information of a user, the second sensor comprising a colorimetric sensor including a photoplethysmogram (PPG) sensor, the PPG sensor including a film disposed on an upper end of the PPG sensor to sense light;
- determining in real time whether the metabolite information satisfies a specified condition; and
- providing information regarding whether the metabolite information satisfies the specified condition and at least one recommendation corresponding to whether the metabolite information satisfies the specified condition in real time,
- wherein the specified condition includes whether fat of the user is burned off, and
- wherein the providing the information and the at least one recommendation includes:
  - according to the metabolite information satisfying the specified condition, providing information indicating that the user's fat is being burned and a recommendation to maintain the exercise state; and
  - according to the metabolite information not satisfying the specified condition, providing information indicating that the user's fat is not burning and a recommendation to change the exercise state.

9. The method of claim 8, wherein the detecting of the event includes:
- detecting a movement of the electronic device; or
- receiving a user input for starting the exercise state.

10. The method of claim 8,
- wherein the specified condition includes whether fat of the user is burned off,
- wherein the metabolite information includes a lactate value or a ketone body value, and
- wherein the determining of whether the metabolite information satisfies the specified condition includes determining whether the user's fat is burned off, based on the lactate value or the ketone body value.

11. The method of claim 10, wherein the providing of the information regarding the exercise state to the user includes:
- providing a first user interface (UI) representing that the user's fat is burned off, when the metabolite information satisfies the specified condition; and
- providing a second UI to make a request to change the exercise state, when the metabolite information does not satisfy the specified condition.

12. The method of claim 8, further comprising:
- detecting completion of the exercise state;
- determining a zone of the exercise state in which the metabolite information satisfies the specified condition; and
- providing a user interface (UI) representing the zone of the exercise state.

13. The method of claim 8, further comprising:
- obtaining heart rate information of the user; and
- determining whether the heart rate information satisfies another specified condition.

14. An electronic device comprising:
- a memory;
- a second sensor comprising a colorimetric sensor including a photoplethysmogram (PPG) sensor; and
- at least one processor coupled to the memory,
- wherein the memory stores instructions that, when executed, cause the at least one processor to:
  - detect an event relating to start of an exercise state,
  - obtain motion information corresponding to the exercise state,
  - obtain, via the PPG sensor, metabolite information of a user, the PPG sensor including a film disposed on an upper end of the PPG sensor to sense light,
  - determine in real time whether the metabolite information satisfies a specified condition,
  - provide information regarding whether the metabolite information satisfies the specified condition and at least one recommendation corresponding to whether the metabolite information satisfies the specified condition in real time,
- wherein the specified condition includes whether fat of the user is burned off, and
- wherein the instructions cause the at least one processor to:
  - according to the metabolite information satisfying the specified condition, provide information indicating that the user's fat is being burned and a recommendation to maintain the exercise state, and
  - according to the metabolite information not satisfying the specified condition, provide information indicating that the user's fat is not burning and a recommendation to change the exercise state.

15. The electronic device of claim 14, wherein the instructions cause the at least one processor to obtain the motion information from an external electronic device.

16. The electronic device of claim 14, wherein the instructions cause the at least one processor to:
- provide a first user interface (UI) representing that fat of the user is burned off, when the metabolite information satisfies the specified condition; and
- provide a second UI to make a request to change the exercise state, when the metabolite information does not satisfy the specified condition.

17. The electronic device of claim 14, wherein the instructions cause the at least one processor to:
- detect completion of the exercise state;
- determine a zone of the exercise state in which the metabolite information satisfies the specified condition; and
- provide a user interface (UI) representing the zone of the exercise state.

18. The electronic device of claim 14, wherein the instructions cause the at least one processor to:
- obtain heart rate information of the user; and
- provide the information regarding the exercise state to the user, based on whether the heart rate information satisfies another specified condition.

* * * * *